United States Patent
Kelly et al.

(10) Patent No.: US 6,503,928 B2
(45) Date of Patent: Jan. 7, 2003

(54) ARYLPIPERIDINE AND ARYL-1,2,5,6-TETRAHYDROPYRIDINE AMIDE DERIVATIVES

(75) Inventors: Michael G. Kelly, Newbury Park, CA (US); Gan Zhang, Plainsboro, NJ (US); Yvette L. Palmer, Yardley, PA (US); Wayne E. Childers, Levittown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/954,784

(22) Filed: Sep. 18, 2001

(65) Prior Publication Data

US 2002/0035263 A1 Mar. 21, 2002

Related U.S. Application Data

(62) Division of application No. 09/459,801, filed on Dec. 13, 1999, now Pat. No. 6,326,381.
(60) Provisional application No. 60/160,088, filed on Dec. 17, 1998.

(51) Int. Cl.$^7$ .................. C07D 401/06; A61K 31/4427
(52) U.S. Cl. ....................... 514/332; 514/357; 546/262; 546/263; 546/337
(58) Field of Search ................ 546/262, 263, 546/337; 514/332, 357

(56) References Cited

PUBLICATIONS

CA 132: 49981, Childers et al. 1999.*

* cited by examiner

*Primary Examiner*—Jane Fan
(74) *Attorney, Agent, or Firm*—Rebecca R. Barrett

(57) ABSTRACT

Compounds of the formula

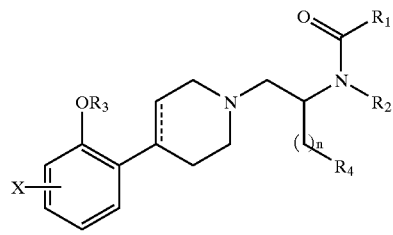

wherein $R_1$, $R_2$, $R_3$, $R_4$, X and n are defined in the specification, are useful for the treatment of anxiety, depression and related CNS disorders, and other related conditions such as the treatment of alcohol and drug withdrawal, sexual dysfunction and Alzheimer's disease.

11 Claims, No Drawings

ARYLPIPERIDINE AND ARYL-1,2,5,6-TETRAHYDROPYRIDINE AMIDE DERIVATIVES

This application is a divisional application of U.S. Ser. No. 09/459,801, filed Dec. 13, 1999, now U.S. Pat. No. 6,326,381 which claims benefit of prior U.S. Provisional application No. 60/160,088, filed Dec. 17, 1998.

BACKGROUND OF THE INVENTION

U.S. Pat. No. 4,882,432 teaches ureas with high 5-HT1A receptor affinities. These compounds, as well as those disclosed in U.S. Pat. No. 4,797,489 are useful for the treatment of CNS disorders.

DESCRIPTION OF THE INVENTION

This invention relates to novel arylpiperidine and aryl-1,2,5,6-tetrahydropyridine amide derivatives which are agonists and antagonists of the 5HT1A receptor subtype. By virtue of their high binding affinity to the 5HT1A receptor, compounds of the present invention are useful for the treatment of central nervous system (CNS) disorders such as depression, anxiety, panic, obsessive-compulsive disorder (OCD), sleep disorders, sexual dysfunction, alcohol and drug addiction, cognition enhancement, Alzheimer's disease, Parkinson's disease, obesity and migraine.

Compounds of the present invention are represented by the general formula (A),

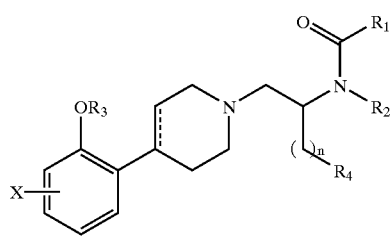

wherein:
$R_1$ is alkyl, cycloalkyl, heterocycloalkyl, alkylcycloalkyl, alkylheterocycloalkyl, aryl or heteroaryl; provided that the point of attachment is a carbon atoms;
$R_2$ is hydrogen, alkyl or $(CH_2)R_5$;
$R_3$ is hydrogen or alkyl;
X is hydrogen, halogen, perhaloalkyl, hydroxy, alkoxy, or perhaloalkoxy;
$R_4$ is aryl or heteroaryl;
R5 is alkyl, alkenyl or alkynyl;
n is an integer from 1 to 3; and the dotted line is an optional double bond, or a pharmaceutical salt thereof.

In some preferred embodiments of the present invention R1 is cycloalkyl. In still other preferred embodiments of the present invention X is 4- or 5-fluoro and more preferably X is 5-fluoro. In other preferred embodiments of the present invention $R_4$ is phenyl or pyridyl.

Alkyl, as used herein refers to straight or branched chain alkyl of 1 to 6 carbon atoms. In some preferred embodiments alkyl is straight chain alkyl of 1–5 carbon atoms and in some embodiments 1–4 carbon atoms. Exemplary alkyl groups include methyl, ethyl, propyl, isopropyl, butyl, isobutyl, t-butyl, pentyl and hexyl. In some preferred embodiments, the alkyl group has from 1 to 5 carbon atoms. In some embodiments of the present invention the alkyl group may be substituted with one or more substituents.

Alkenyl, as used herein refers to straight or branched chain alkyl of 2 to 6 carbon atoms having at least one carbon-carbon double bond. Exemplary alkenyl groups include ethylene and propylene. In some embodiments of the present invention the alkenyl group may be substituted with one or more substituents.

Alkynyl, as used herein refers to straight or branched chain alkyl of 2 to 6 carbon atoms having at least one carbon-carbon triple bond. Exemplary alkenyl groups include ethynyl and propynyl. In some embodiments of the present invention the alkynyl group may be substituted with one or more substituents.

Cycloalkyl, as used herein refers to monocyclic alkyl group having from 3 to 8 carbons. Cycloalkyl groups may be substituted or unsubstituted. In some preferred embodiments of the present invention the cycloalkyl group may be substituted with one to three substituents. A preferred substitution of cycloalkyl is alkyl of 1 to 4 carbon atoms.

Aryl, as used herein refers to mono or bicyclic aromatic ring having from 6 to 10 carbon atoms. Monocyclic rings preferably have 6 members and bicyclic rings preferably have 8, 9 or 10 membered ring structures. Exemplary aryl groups include phenyl and naphthyl. Aryl may be substituted with from one to three substituents. Heteroaryl, as used herein refers to 5 to 10 membered mono or bicyclic aromatic rings having from 1 to 3 heteroatoms selected from N, O and S. Monocyclic rings preferably have 5 or 6 members and bicyclic rings preferably have 8, 9 or 10 membered ring structures. Exemplary heteroaryls include pyrrolyl, furyl, thienyl, imidazolyl, pyrazolyl, oxazolyl, isoxazoly, thiazolyl, isothiazolyl, pyridyl, pyrazinyl, pyrimidinyl, indolyl, quinolyl and isoquinoly. Preferred heteroaryl groups include pyridyl, furyl and thienyl. Most preferred heteroaryls include 2-, 3- and 4-pyridyl, 2- and 3-furyl and 2- or 3-thienyl. Heteroaryls may also be substituted with from one to three substituents.

Halogen as used herein includes fluorine, chlorine, iodine and bromine.

Suitable substituents, unless otherwise noted, include halogen, alkyl, hydroxy, alkoxy, amino, amido, nitro, alkylamino, alkylamido, perhaloalkyl, carboxyalkyl, carboxy, carbamide, dialkylamino and aryl.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, alkylcycloalkyl is an alkyl-cycloalkyl group in which alkyl and cycloalkyl are as previously described.

Pharmaceutically acceptable salts are the acid addition salts which can be formed from a compound of the above general formula and a pharmaceutically acceptable acid such as phosphoric, sulfuric, hydrochloric, hydrobromic, citric, maleic, succinic, fumaric, acetic, lactic, nitric, sulfonic, p-toluene sulfonic, methane sulfonic acid, and the like.

The compounds of this invention contain a chiral center, providing for various seteroisomeric forms of the compounds such as racemic mixtures as well as the individual optical isomers. The individual isomers can be prepared directly or by asymmetric or stereospecific synthesis or by conventional separation of optical isomers from the racemic mixture.

Compounds of formula A and intermediates 4-(halo-2-methoxy-phenyl)-piperidines F or 4-(halo-2-methoxy-phenyl)-1,2,5,6-tetrahydropyridines H of the present invention can be prepared by conventional methods by those skilled in the organic synthesis. For example, in Scheme I, metal-halogen exchange of an appropriately substituted aryl halide B with a base, such as butyllithium, forms a carboanion, and treatment of the resulting mixture with an N-protected-4-piperidone C affords a tertiary alcohol D. An example of the nitrogen protecting group (R$^x$)? of the 4-piperidone is benzyl, which can he removed by hydrogenation to afford amine G. Dehydration of G with an acid, such as sulfuric acid can provide the desired 4-(halo-2-methoxy-phenyl)-1,2,5,6-tetra-hydropyridine H. Dehydration of the tertiary alcohol D, removal of the nitrogen protecting group and hydrogenation of the double bond can afford 4-(halo-2-methoxy-phenyl)-piperidine F.

The des-halo intermediates 4-(2-methoxyphenyl)-piperidine F (X=H) and 1,2,3,6-tetra hydro-4-(2-methoxyphenyl)-pyridine H (X=H) are both known compounds and may be prepared by the following literature procedures:

Van Wijngaarden Ineke et al, J. Med. Chem., (1988), 31(10), 1934–1940.
Perregaard Jens et al., J. Med. Chem., (1995), 38(11), 1998–2008.
Modica Maria et al., J. Med. Chem., (1997), 40(4), 574–585.
Solyom Sandor et al., Heterocycles, (1995), 41(6), 1139–1168.

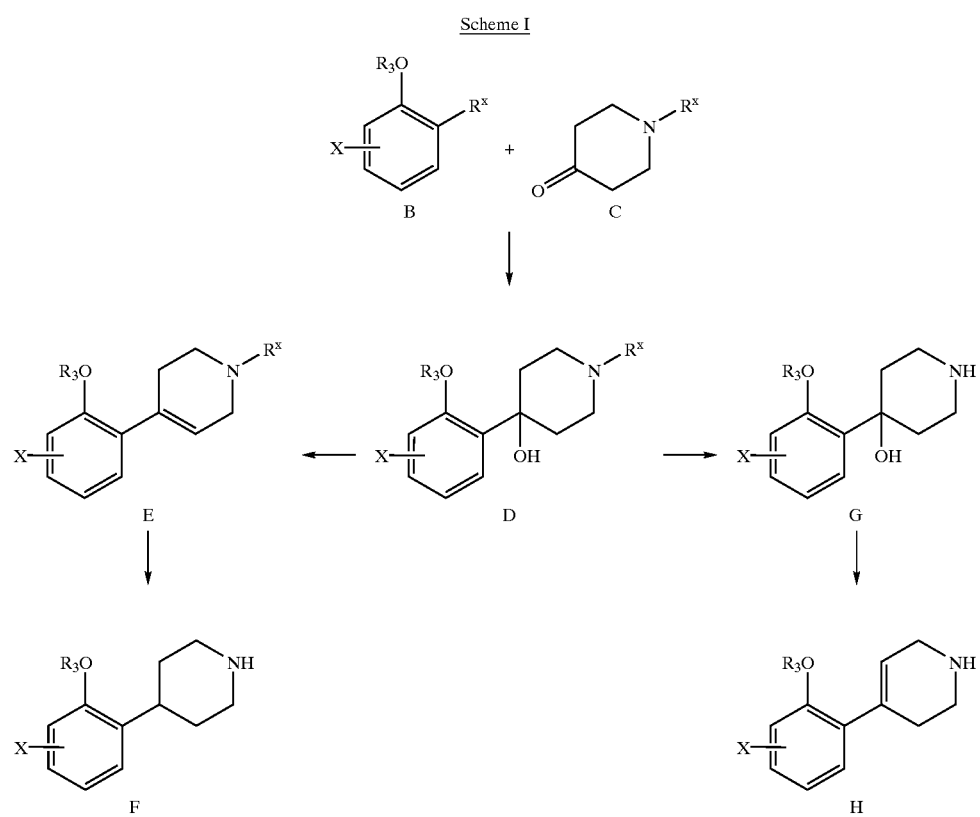

Coupling of 4-(X-2-methoxy-phenyl)-piperidine F or 4-(X-2-methoxy-phenyl)-1,2,5,6-tetrahydropyridine H with an N-protected-N-alkyl aminoacid (I) in the presence of activating reagents, such as 1-(3-dimethylaminopropyl)-3-ethyl-carbodiimide hydrochloride (DEAC), 1-hydroxybenzotriazole hydrate (HOBT), 4-methylmorpholine (NMO) forms amide J (Scheme II). The protecting group R is of the urethane type, preferably tert-butyloxycarbonyl which may be removed by the action of an acid. After deprotection, the amide may be reduced to an amine M with a reducing reagent such as lithium aluminum hydride (LAH) or diborane, and subsequently acylated to give compound A.

Scheme II

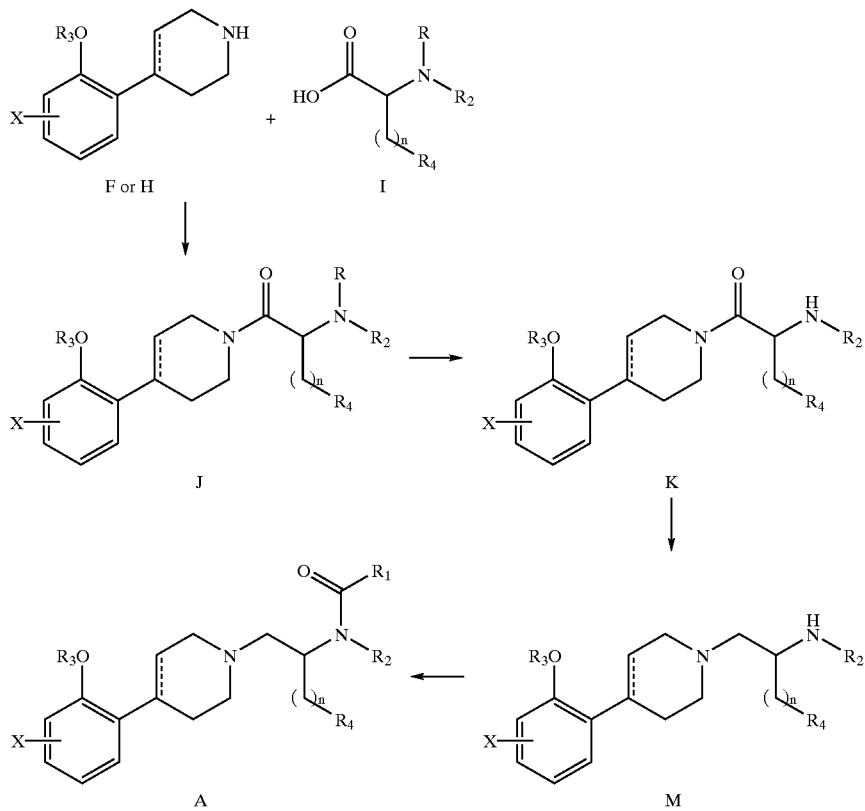

The following non-limiting specific examples are included to illustrate the synthetic procedures used for preparing compounds of formula A. In these examples, all chemicals and intermediates are either commercially available or can be prepared by standard procedures found in the literature or are known to those skilled in the art of organic synthesis. Several preferred embodiments are described to illustrate the invention. However, it should be understood that the invention is not intended to be limited to the specific embodiments.

EXAMPLE 1

1-Methyl-cyclohexanecarboxylic Acid {(1R)-1-Benzyl-2-[4-(5-fluoro-2-methoxy-phenyl)-piperidine-1-yl]-ethyl}-methyl-amide a) 1-Benzyl-4-(5-fluoro-2-methoxy-phenyl)-4-hydroxypiperidine To a solution of 9.8 mL (24 mmole) butyllithium (2.5 M solution in hexane) in diethylether (20 mL) under $N_2$ at −78° C. was slowly added 2-bromo-5-fluoroanisole (5.0 g, 24 mmole) in diethylether (5 mL). The mixture was allowed to warm up to −50° C. At this point, 1-benzyl-4-piperidone (4.62 g, 24.4 mmole) in diethylether (3 mL) was added. The resulting mixture was allowed to stirred at −50° C. for 30 minutes, and then warmed to room temperature. The reaction was quenched by dropwise addition of saturated $NH_4Cl$ solution. The mixture was then transferred to a separatory funnel, the layers were separated and the aqueous was extracted three times with EtOAc. The combined organic phase was dried over $Na_2SO_4$, filtered and concentrated. Flash chromatography (elution with 7:3 EtOAc-hexanes) afforded 5.27 g (68%) of 1-benzyl-4-(5-fluoro-2-methoxy-phenyl)-4-hydroxypiperidine as a yellow oil.

b) 1-Benzyl-4-(5-fluoro-2-methoxy-phenyl)-1,2,5,6-tetrahydropyridine

To a solution of 1-benzyl-4-(5-fluoro-2-methoxy-phenyl)-4-hydroxypiperidine (1.01 g 3.20 mmole) in acetic acid (40 mL) at room temperature was added 2 drops of concentrated sulfuric acid. The resulting solution was heated to reflux, and the mixture stirred for 2 days. The mixture was cooled to room temperature and diluted with EtOAc (100 mL) and water (100 mL). The solution was basified with 50% NaOH solution until pH=10. The layers were separated and the organics washed with brine. The combined aqueous layers were extracted three times with EtOAc (50 mL). The combined organic layers were dried over $Na_2SO_4$ and concentrated. Flash chromatography (elution with 1:1 EtOAc-hexane) to give 0.62 g (65%) of 1-benzyl-4-(5-fluoro-2-methoxy-phenyl)-1,2,5,6-tetrahydropyridine as a yellow oil.

c) 1-Formyl-4-(5-fluoro-2-methoxy-phenyl)-piperidine

10% Palladium on carbon (0.62 g) was added to a methanolic solution (20 mL) of 1-benzyl-4-(5-fluoro-2-methoxy-phenyl)-1,2,5,6-tetrahydropyridine (0.62 g, 2.1 mmole) The solution was purged with $N_2$ for 5 minutes followed by dropwise addition of formic acid (2 mL, 88%) and the resulting mixture was stirred at room temperature for two days. The mixture was filtered through celite, and concentrated to afford 0.44 g (90%) of 1-formyl-4-(5-fluoro-2-methoxy-phenyl)-piperidine as a colorless oil.

Elemental Analysis for: $C_{13}H_{16}FNO_2 \cdot 0.09(C_3H_7NO)$; Calculated: C, 65.81; H, 6.80; N, 5.90; Found: C, 65.36; H, 6.87; N, 6.26.

d) 4-(5-Fluoro-2-methoxy-phenyl)-piperidine

The crude product of 1-formyl-4-(5-fluoro-2-methoxy-phenyl)-piperidine (0.80 g, 3.4 mmole) was dissolved in HCl (16 mL, 0.5 N) and MeOH (5 mL), and the mixture was brought to reflux for 16 hours. The mixture was cooled to room temperature and basified with NaOH (2.5 N), and extracted with EtOAc (3×25 mL) to give 4-(5-fluoro-2-methoxy-phenyl)-piperidine which was used directly without further purification.

e) (R)-{1-Benzyl-2-[4-(5-fluoro-2-methoxy-phenyl)-piperidin-1-yl]-2-oxo-ethyl}-methyl-carbamic Acid tert-Butyl Ester The above product of 4-(5-fluoro-2-methoxy-phenyl)-piperidine was dissolved in N,N-dimethylformamide (10 mL) at 0° C. To the resulting solution, 0.70 g (2.5 mmole) of 2-[N-methyl-N-(tert-butoxycarbonyl)-amino]-3-phenyl-propionic acid in a minimal amount of DMF was added, followed by DEAC (0.48 g, 2.5 mmole), HOBT (0.41 g, 2.5 mmole) and NMO (0.37 mL, 3.4 mmole) and the mixture was stirred overnight (the reaction temperature was slowly allowed to warm up to room temperature). The reaction mixture was diluted with water (50 mL) and EtOAc (50 mL) and the layers separated. The aqueous layer was washed with HCl (1 N), saturated NaHCO$_3$, and the combined aqueous layers were extracted three times with EtOAc. The combined organic layers were dried over NA$_2$SO$_4$ and concentrated. Flash chromatography, gradient elution with 1:4 EtOAc-hexane to 3:7 EtOAc-hexane to afford (R)-{1-benzyl-2-[4-(5-fluoro-2-methoxy-phenyl)-piperidin-1-yl]-2-oxo-ethyl}-methyl-carbamic acid tert-butyl ester as a yellow oil.

f) (2R)-1-[4-(5-Fluoro-2-methoxy-phenyl)-piperazin-1-yl]-2-methylamino-3-phenyl-propan-1-one hydrochloride The above product of (R)-{1-benzyl-2-[4-(5-fluoro-2-methoxy-phenyl)-piperidin-1-yl]-2-oxo-ethyl}-methyl-carbamic acid tert-butyl ester was dissolved in 4 M HCl/dioxane (10 mL) and the resulting solution brought to reflux. After stirring overnight. the mixture was cooled to room temperature and the solvent evaporated to provide 0.38 g (22% for three steps) of the titled product.

g) {(1R)-1-Benzyl-2-[4-(5-fluoro-2-methoxyphenyl)-piperidin-1-yl]-ethyl}-methyl-amine To a mixture of (2R)-1-[4-(5-fluoro-2-methoxy-phenyl)-piperazin-1-yl]-2-methyl-amino-3-phenyl-propan-1-one hydrochloride (0.38 g, 0.93 mmole) in tetrahydrofuran (20 mL) at 0° C. under N$_2$ atmosphere was added triethylamine (0.14 mL, 1.0 mmol), followed by the dropwise addition of lithium aluminum hydride (1.9 mL, 1.9 mmole 1 M solution in THF). After addition, the cooling bath was removed and the mixture stirred at room temperature for 2.5 hours. The reaction was quenched by slow addition of saturated NH$_4$Cl solution and the mixture was filtered through a celite pad. The solution was concentrated to afford the titled compound as a yellow oil and was used without further purification.

h) 1-Methyl-cyclohexanecarboxylic Acid {(1R)-1-Benzyl-2-[4-(5-fluoro-2-methoxy-phenyl)-piperidin-1-yl]-ethyl}-methyl-amide Under a N$_2$ atmosphere, a solution of {(1R)-1-benzyl-2-[4-(5-fluoro-2-methoxy-phenyl)-piperidin-1-yl]-ethyl}-methyl-amine (0.12 g, 0.33 mmole) and triethylamine (0.10 mL, 0.74 mmole) in dichloromethane (10 mL) was cooled to 0° C. To the solution, 1-methyl-1-cyclohexanecarboxylicacid chloride (93 mg, 0.58 mmole) in a minimal amount of dichloromethane was added. The resulting mixture was stirred at 0° C. overnight. The solvent was evaporated and the residue dissolved in EtOAc (50 mL) and water (50 mL). The layers were separated, the organics washed with water (2×50 mL) and brine and dried over Na$_2$SO$_4$, filtered and concentrated. Flash chromatography (elution with 1:3 EtOAc-hexane) gave 0.14 g (88% yield) of 1-methyl-cyclohexanecarboxylic acid {(1R)-1-benzyl-2-[4-(5-fluoro-2-methoxy-phenyl)-piperidin-1-yl]-ethyl}-methylamide. An ethanolic solution of the product was heated to gentle reflux and 1 equivalent of fumaric acid in hot ethyl alcohol solution was added to afford the fumarate salt of the titled compound as a white solid.

m.p. 160–165 ° C. Elemental Analysis for: $C_{30}H_{41}FN_2O_2 \cdot 1.0C_4H_{4O4}$; Calculated: C, 68.43; H, 7.60; N, 4.69; Found: C,68.38; H,7.69; N, 4.33.

EXAMPLE 2

1-Methyl-cyclohexanecarboxylic Acid {(1R)-1-Benzyl-2-[4-(5-fluoro-2-methoxy-phenyl)-1,2,5,6-tetrahydro-4H-pyridin-1-yl]-ethyl}-methyl-amide a) 4-(5-Fluoro-2-methoxy-phenyl)-4-hydroxypiperidine In a round bottom flask at room temperature was placed with 1.95 g (6.18 mmole) 1-benzyl-4-(5-fluoro-2-methoxy-phenyl)-4-hydroxypiperidine, dry MeOH (40 mL), and the system purged with N$_2$ for 5 min. To the solution, 1.95 g of 10% palladium on carbon was added. The system was again purged with N$_2$ for 5 minutes followed by addition of 2 mL formic acid (88%). The resulting mixture was stirred at room temperature under N$_2$ for one day. At this point, a further 2 mL of formic acid (88%) was added. The reaction was continued for 2.5 days. The mixture was filtered through celite, and concentrated to afford of 4-(5-fluoro-2-methoxy-phenyl)-4-hydroxypiperidine (0.95 g, 69% yield) as a yellow oil.

b) 4-(5-Fluoro-2-methoxy-phenyl)-1,2,5,6-tetrahydropyridine

To a solution of 4-(5-fluoro-2-methoxy-phenyl)-4-hydroxypiperidine (0.56 g, 2.5 mmole) in acetic acid (20 mL) at room temperature was added 2 drops of concentrated sulfuric acid and the resulting solution heated to reflux for 2 days. The reaction mixture was cooled to room temperature and diluted with EtOAc (50 mL) and water (50 mL). The solution was basified with 50% NaOH solution until PH=10, the layers separated and the organic layer was washed with brine (25 mL). The combined aqueous layers were extracted three times with EtOAc (3×25 mL), and the combined organic layers were dried over Na$_2$SO$_4$ and concentrated to afford 0.49 g (95% yield) of 4-(5-fluoro-2-methoxy-phenyl)-1,2,5,6-tetrahydropyridine as a yellow oil.

c) (R)-{1-Benzyl-2-[4-(5-fluoro-2-methoxy-phenyl)-1,2,5,6-tetrahydro pyridin-1-yl]-2-oxo-ethyl}-methyl-carbamic Acid tert-Butyl Ester The crude product of 4-(5-fluoro-2-methoxy-phenyl)-1,2,5,6-tetrahydropyridine (0.49 g, 2.4 mmole) was dissolved in N,N-dimethylformamide (10 mL) at 0° C., and the resulting solution treated with 2-[N-methyl-N-(tert-butoxycarbonyl)-amino]-3-phenyl-propionic acid (0.73 g, 2.6 mmole) in a minimal amount of DMF, DEAC (0.50 g, 2.6 mmole), HOBT (0.42 g, 3.1 mmole) and NMO (0.40 mL, 3.6 mmole). The mixture was stirred overnight, and was diluted with water (50 mL) and EtOAc (50 mL). The layers were separated and the organic layer was washed with HCl (1N), saturated NaHCO$_3$, and the combined aqueous washings were extracted three times with EtOAc (3×25 mL). The combined organic layers were dried over Na$_2$SO$_4$ and concentrated to afford (R)-{1-benzyl-2-[4-(5-fluoro-2-methoxy-phenyl)-1,2,5,6-tetrahydropyridin-1-yl]-2-oxo-ethyl}-methyl-carbamic acid tert-butyl ester as a yellow oil.

d) (2R)-1-[4-(5-Fluoro-2-methoxy-phenyl)-1,2,5,6-tetrahydropyridin-1-yl]-2-methylamino-3-phenyl-propan-1-one hydrochloride The crude product of (R)-{1-benzyl-2-[4-(5-fluoro-2-methoxy-phenyl)-1,2,5,6-tetrahydropyridin-1-yl]-2-oxoethyl}-methyl-carbamic acid tert-butyl ester was dissolved in 10 mL 4 M HCl/dioxane solution and the resulting mixture brought to reflux. After overnight stirring, the mixture was cooled to room temperature and the solvent evaporated to provide 0.62 g (65% yield for two steps) of the titled product.

e) {(1R)-1-Benzyl-2-[4-(5-fluoro-2-methoxy-phenyl)-1,2,3,6-tetrahydro pyridin-1-yl]-ethyl}-methyl-amine To a mixture of (2R)-1-[4-(5-fluoro-2-methoxy-phenyl)-1,2,3,6-tetrahydropyridin-1-yl]-2-methylamino-3-phenyl-propan-1-one hydrochloride (0.41 g, 1.0 mmole) in 20 mL of tetrahydrofuran at 0° C. under $N_2$ was added of triethylamine (0.14 mL, 1.0 mmol), followed by slow addition of 1.9 mL (1.9 mmole) lithium aluminum hydride (1 M solution in THF). After addition, the cooling bath was removed and the mixture was stirred at room temperature for 2.5 hours. The reaction was quenched by the slow addition of saturated $NH_4Cl$ solution and the mixture was filtered through a celite pad. The solution was concentrated to afford 0.36 g (100% {(1R)-1-benzyl-2-[4-(5-fluoro-2-methoxy-phenyl)-1,2,5,6-tetrahydropyridin-1-yl]-ethyl}-methyl-amine as a yellow oil which was used without further purification.

f) 1-Methyl-cyclohexanecarboxylic Acid {(1R)-1-Benzyl-2-[4-(5-fluoro-2-methoxy-phenyl)-1,2,5,6-tetrahydro-4H-pyridin-1-yl]-ethyl}-methyl-amide Under a $N_2$ atmosphere, a solution of {(1R)-1-benzyl-2-[4-(5-fluoro-2-methoxy-phenyl)-1,2,5,6-tetrahydropyridine-1-yl]-ethyl}-methyl-amine (0.18 g, 0.49 mmole) and triethylamine (0.14 mL, 1.0 mmole) in dichloromethane (10 mL) was cooled to 0° C. To the solution, 1-methyl-1-cyclohexanecarboxylicacid chloride (0.10 g, 0.59 mmole) in 1 mL dichloromethane was added and the resulting mixture was stirred at 0° C. to room temperature (ice melt) overnight. The solvent was evaporated and the residue dissolved in EtOAc (50 mL) and water (50 mL). The layers were separated and the organics washed with water (50 mL), brine (25 mL) and dried over $Na_2SO_4$, filtered and concentrated. Flash chromatography (elution with 1:4 EtOAc-hexane) gave 0.13 g (55% yield) of the titled compound. An ethanolic solution of the product was heated to gentle reflux and 1 equivalent of fumaric acid in hot ethyl alcohol solution was added to afford the fumarate salt of the titled compound as a white solid.

m.p. 146–151° C. Elemental Analysis for: $C_{30}H_{39}FN_2O_2 \cdot 1.0C_4H_4O_4$; Calculated: C, 68.67; H, 7.29; N, 4.71; Found: C, 67.07; H, 7.08; N, 4.54.

EXAMPLE 3

(R)-Cyclohexanecarboxylic Acid {1-Benzyl-2-[4-(2-methoxy-phenyl)-3,6-dihydro-2H-pyridin-1-yl]-ethyl}-amide To a solution of Boc-D-phenylalanine (2.0 g, 7.54 mmol), DEAC (1.45 g, 7.54 mmol), and HOBT (1.53 g, 11.3 mmol) in DMF (20 mL) at 0° C. was added of 1,2,3,6-tetrahydro-4-(2-methoxyphenyl)pyridine (1.87 g, 8.29 mmol), followed by the addition of NMO (1.4 mL, 12.8 mmol). The mixture was stirred under nitrogen for 16 hours at ambient temperature, diluted with ethyl acetate (100 mL) and washed with 0.1 N HCl (25 mL), saturated $NaHCO_3$ (25 mL), $H_2O$ (25 mL) and brine (25 mL). The organic phase was dried over anhydrous $Na_2SO_4$, filtered and concentrated under vacuum to yield the required product (100% yield). This was stirred in 40 mL 4.0M HCl/dioxane overnight and concentrated to afford the hydrochloride salt of the deprotected amine. The amide was dissolved in THF (50 mL) and reduced at 0° C. by the addition of 1.0M LAH/THF (23 mL). After Stirring overnight at room temperature, the reaction was quenched with the addition of saturated $NH_4Cl$, filtered through celite, dried over anhydrous $Na_2SO_4$, filtered and concentrated to yield the required product. Cyclohexanecarboxylicacid chloride (0.61 g, 4.13 mmol) was added dropwise to a solution of the amine (1.21 g, 3.75 mmol) and triethylamine (1.1 mL, 7.5 mmol) in dichloromethane (20 mL) at 0° C. The mixture was allowed to stir under nitrogen overnight at ambient temperature, concentrated under vacuum, diluted with ethyl acetate (50 mL) and washed with $H_2O$ (50 mL) then brine (25 mL). The organic phase was dried over anhydrous $Na_2SO_4$, filtered and concentrated under vacuum to yield crude product. Purification by flash chromatography (elution with ethyl acetate/hexanes) yielded 0.47 g of the above titled free base. The fumarate salt was prepared and crystallized yielding 0.28 g of the title compound as a pale yellow solid, m.p. 146–148° C.

$[\alpha]_{25/D}$=−11.95° (MeOH, 8.4 mg/mL); Elemental Analysis for: $C_{28}H_{36}N_2O_2 \cdot 2.0C_4H_4O_4 \cdot 0.5H_2O$; Calculated: C, 64.18; H, 6.73; N, 4.16; Found: C, 64.06; H, 6.74; N, 4.17.

EXAMPLE 4

(R)-1-Methyl-cyclohexanecarboxylic Acid {1-Benzyl-2-[4-(2-methoxy-phenyl)-3,6-dihydro-2H-pyridin-1-yl]-ethyl}-amide 1-Methyl-cyclohexanecarboxylicacid chloride (0.66 g, 4.13 mmol) was added dropwise to a solution of the amine (1.21(g, 3.75 mmol, prepared exactly as described in example 3 above) and triethylamine (1.1 mL, 7.5 mmol) in dichloromethane (20 mL) at 0° C. The mixture was allowed to stir under nitrogen overnight at ambient temperature, was concentrated under vacuum, diluted with ethyl acetate (50 mL), washed with $H_2O$ (25 mL) and brine. The organic phase was dried over anhydrous $Na_2SO_4$, filtered and concentrated under vacuum to yield crude product. Purification by flash chromatography (elution with ethyl acetate/hexanes) yielded 0.36 g of the above titled free base. The fumarate salt was prepared and crystallized yielding 0.28 g of the title compound as a pale yellow solid, m.p. 102–104° C.

$[\alpha]_{25/D}$=12.19° (MeOH, 7.2 mg/mL); Elemental Analysis for: $C_{29}H_{38}N_2O_2 \cdot 1.0C_4H_4 \cdot 1.5H_2O$; Calculated: C, 67.21; H, 7.69; N, 4.75; Found: C, 66.84; H, 7.25; N, 4.43.

EXAMPLE 5

(R)-1-Methyl-cyclohexanecarboxylic Acid {1-Benzyl-2-[4-(2-methoxy-phenyl)-piperidin-1-yl]-ethyl}-amide To a solution of Boc-D-phenylalanine (2.0 g, 7.54 mmol), DEAC (1.45 g, 7.54 mmol), and HOBT (1.53 g, 11.3 mmol) in DMF (20 mL) at 0° C. was added 4-(2-methoxyphenyl)piperidine (1.88 g, 8.29 mmol) followed by the addition of NMO (1.4 mL, 12.8 mmol). The mixture was allowed to stir under nitrogen overnight at ambient temperature, diluted with ethyl acetate (50 mL) and washed with 0.1N HCl (20 mL), saturated $NaHCO_3$ (20 mL), $H_2O$ (25 mL) and brine. The organic phase was dried over anhydrous $Na_2SO_4$, filtered and concentrated under vacuum to yield the required product (100%). This was stirred in 4.0M HCl/dioxane (40 mL) overnight and concentrated to afford the hydrochloride salt of the free amine. The amide was dissolved in THF (30 mL) and reduced by the addition of 1.0M LAH/THF (23 mL) at 0° C. After stirring overnight, the reaction was quenched by the addition of saturated NH$_4$Cl, filtered through celite, dried over anhydrous Na$_2$SO$_4$, filtered and concentrated to yield the required product. 1-Methylcyclohexanecarboxylicacid chloride was added to a solution of the amine (1.22 g, 3.76 mmol) and triethylamine (1.1 mL, 7.5 mmol) in dichloromethane (20 mL) at 0° C. The reaction mixture was allowed to stir under nitrogen overnight at ambient temperature, concentrated under vacuum, diluted with ethyl acetate (50 mL) and washed with H$_2$O (2×25 mL) then brine. The organic phase was dried over anhydrous Na$_2$SO$_4$, filtered and concentrated under vacuum to yield crude product. Purification by flash chromatography (elution with ethyl acetate/hexanes) yielded 1.1 g of the titled free base. The fumarate salt was prepared and crystallized yielding 0.81 g of the title compound as a pale yellow solid, m.p. 77–79° C.

$[\alpha]_{25/D}$=10.37° (MeOH, 10.0 mg/mL); Elemental Analysis for: C$_{29}$H$_{40}$N$_2$O$_2$.2.0C$_4$H$_4$O$_4$; Calculated: C, 65.28; H, 7.11; N, 4.11; Found: C, 65.28; H, 7.35; N, 4.16.

EXAMPLE 6

(R)-Cyclohexanecarboxylic Acid {1-Benzyl-2-[4-(2-methoxy-phenyl)-piperidin-1-yl]-ethyl}-amide 1,2,3,6-Tetrahydro-4-(2-methoxyphenyl)pyridine (1.87 g, 8.29 mmol) was added to a solution of Boc-D-phenylalanine (2.0 g, 7.54 mmol), DEAC (1.45 g, 7.54 mmol), and 1.53 g (11.3 mmol) of HOBT in DMF (20 mL) at 0° C., followed by the addition of NMO (1.4 mL, 12.8 mmol). The mixture was stirred under nitrogen overnight at ambient temperature, then diluted with ethyl acetate (50 mL), washed with 0.1N HCl (15 mL), saturated NaHCO$_3$, H$_2$O and finally brine. The organic phase was dried over anhydrous Na$_2$SO$_4$, filtered and concentrated under vacuum to yield (100%) crude product. This was stirred in 4.0M HCl/dioxane (40 mL) overnight and concentrated to afford the amine hydrochloride salt. The amide was dissolved in THF (50 mL) and reduced over 16 hours at 0° C. by the addition of 1.0M LiAlH$_4$/THF (23 mL). The reaction was quenched with the addition of saturated NH$_4$Cl, filtered through celite, dried over anhydrous Na$_2$SO$_4$, filtered and concentrated to yield the required product (1.22 g). Cyclohexanecarboxylic acid chloride (0.61 g, 4.13 mmol) was added to a solution of (1.22 g, 3.76 mmol) of crude amine and triethylamine (1.1 mL, 7.5 mmol) in dichloromethane (20 mL) at 0° C. The mixture was allowed to stir under nitrogen overnight at ambient temperature, then concentrated under vacuum, diluted with ethyl acetate (50 mL) and washed with H$_2$O (2×50 mL) then brine (50 mL). The organic phase was dried over anhydrous Na$_4$SO$_4$, filtered and concentrated under vacuum to yield the required amide. Purification by flash chromatography (elution with ethyl acetate/hexanes) yielded 0.53 g of the titled free base. The fumarate salt was prepared and crystallized yielding 0.19 g of the title compound as a pale yellow solid, m.p. 103–105° C.

$[\alpha]_{25/D}$=−10.5° (MeOH, 8.2 mg/mL); Elemental Analysis for: C$_{28}$H$_{38}$N$_2$O$_2$.1.0C$_4$H$_4$O$_4$.0.75H$_2$O; Calculated: C, 68.12; H, 7.77; N, 4.96; Found: C, 68.05; H, 7.71; N, 4.94.

EXAMPLE 7

1-Methyl-cyclohexanecarboxylic Acid {(1R)-2-[4-(2-Methoxy-phenyl)-piperidin-1-yl]-1-pyridin-3-ylmethyl-ethyl}-amide 1,2,3,6-Tetrahydro-4-(2-methoxyphenyl)pyridine (1.0 g, 4.39 mmol) was added to a solution of N-Boc-3'-(3'-pyridyl)-D-alanine (1.17 g, 4.39 mmol), DAEC (0.84 g, 4.39 mmol), and HOBT (0.77 g, 1.3 eq.) in DMF (20 mL) at 0° C., followed by the addition of NMO (0.7 mL, 1.5 eq.). The mixture was stirred under nitrogen overnight at ambient temperature, then diluted with ethyl acetate (50 mL), washed with 0.1N HCl (15 mL), saturated NaHCO$_3$, H$_2$O and finally brine. The organic phase was dried over anhydrous Na$_2$SO$_4$, filtered and concentrated under vacuum to yield (100%) crude product. This was stirred in 4.0M HCl/dioxane (40 mL) overnight and concentrated to afford the amine hydrochloride salt, from which the free base was liberated by treatment with a saturated NaHCO$_3$ solution. The amide was dissolved in THF (50 mL) and the resulting solution treated with the dropwise addition of BH$_3$.THF (10 equivalents) and the mixture was refluxed for 16 hours. After cooling, the reaction was terminated by the addition of 2N HCl, and after stirring for eight hours the mixture was concentrated in vacuo. The aqueous solution was made basic and the product was extracted into EtOAc (3×25 mL), the combined organics were washed with water (50 mL), brine, separated and dried over anhydrous Na$_2$SO$_4$. Filtration and concentration under vacuum gave the required product (100% yield). 1-Methylcyclohexanecarboxylic acid chloride (0.17 g, 1.1 mmol) was added to a solution of (0.35 g, 1.1 mmol) of crude amine and triethylamine (0.3 mL, 2.2 mmol) in dichloromethane (5 mL) at 0° C. The mixture was allowed to stir under nitrogen overnight at ambient temperature, then concentrated under vacuum, diluted with ethyl acetate (50 mL) and washed with H$_2$O (2×50 mL ) then brine (50 mL). The organic phase was dried over anhydrous Na$_2$SO$_4$, filtered and concentrated under vacuum to yield the required amide. Purification by flash chromatography (elution with ethyl acetate/hexanes) yielded 0.43 g of the titled free base. The fumarate salt was prepared and crystallized yielding 0.29 g of the title compound as a pale yellow solid, m.p. 99–101° C.

Elemental Analysis for: C$_{28}$H$_{39}$N$_3$O$_2$.1.5C$_4$H$_4$O$_4$; Calculated: C, 65.47; H, 7.27; N, 6.74; Found: C, 65.65; H, 7.70; N, 6.67.

EXAMPLE 8

1-Methyl-cyclohexanecarboxylic Acid {(1R)-2-[4-(2-Methoxy-phenyl)-piperidin-1-yl]-1-pyridin-4-ylmethyl-ethyl}-amide 1,2,3,6-Tetrahydro-4-(2-methoxyphenyl)pyridine (1.0 g, 4.39 mmol) was added to a solution of N-Boc-3'-(4'-pyridyl)-D-alanine (1.17 g, 4.39 mmol), DAEC (0.84 g, 4.39 mmol), and HOBT (0.77 g, 1.3 eq.) in DMF (20 mL) at 0° C., followed by the addition of NMO (0.7 mL, 1.5 eq.). The mixture was stirred under nitrogen overnight at ambient temperature, then diluted with ethyl acetate (50 mL), washed with 0.1N HCl (15 mL), saturated NaHCO$_3$, H$_2$O and finally brine. The organic phase was dried over anhydrous Na$_2$SO$_4$, filtered and concentrated under vacuum to yield (1.9 g, 100%) crude product. This was stirred in 4.0M HCl/dioxane (40 mL) overnight and concentrated to afford the amine hydrochloride salt, from which the free base was liberated by treatment with a saturated NaHCO$_3$ solution. The amide (0.5 g, 1.47 mmol) was dissolved in THF (50 mL) and the resulting solution treated with the dropwise addition of BH$_3$.THF (10 equivalents) and the mixture was refluxed for 16 hours. After cooling, the reaction was terminated by the addition of 2N HCl, and after stirring for eight hours the mixture was concentrated in vacuo. The aqueous solution was made basic and the product was extracted into EtOAc (3×25 mL), the combined organics were washed with water (50 mL), brine, separated and dried over anhydrous $Na_2SO_4$. Filtration and concentration under vacuum gave the required product (0.33 g, 70% yield). 1-Methylcyclohexane carboxylic acid chloride (0.16 g, 1.0 equivalents) was added to a solution of (0.33 g, 1.0 mmol) of crude amine and triethylamine (0.3 mL, 2.2 mmol) in dichloromethane (5 mL) at 0° C. The mixture was allowed to stir under nitrogen overnight at ambient temperature, then concentrated under vacuum, diluted with ethyl acetate (50 mL) and washed with $H_2O$ (2×50 mL) then brine (50 mL). The organic phase was dried over anhydrous $Na_2SO_4$, filtered and concentrated Linder vacuum to yield the required amide. Purification by flash chromatography (elution with ethyl acetate/hexanes) yielded 0.33 g of the titled free base. The fumarate salt was prepared and crystallized yielding 0.29 g of the title compound as a white solid, m.p. 108–110° C. Elemental Analysis for: $C_{28}H_{39}N_3O_2.1.5C_4H_4O_4.0.5H_2O$; Calculated: C, 64.54; H, 7.33; N, 6.64; Found: C, 64.34; H, 7.31; N, 6.43.

EXAMPLE 9

Cyclohexanecarboxylic Acids {(1R)-2-[4-(2-Methoxy-phenyl)-piperidin-1-yl]-1-pyridin-3-ylmethyl-ethyl}-methyl-amide 1,2,3,6-Tetrahydro-4-(2-Methoxyphenyl)pyridine (1.0 g, 4.39 mmol) was added to a solution of N-Boc-3'-(3'-pyridyl)-D-alanine (1.17 g, 4.39 mmol), DAEC (0.84 g, 4.39 mmol), and HOBT (0.77 g, 1.3 eq.) in DMF (20 mL) at 0° C., followed by the addition of NMO (0.7 mL, 1.5 eq.). The mixture was stirred under nitrogen overnight at ambient temperature, then diluted with ethyl acetate (50 mL), washed with 0.1N HCl (15 mL), saturated $NaHCO_3$, $H_2O$ and finally brine. The organic phase was dried over anhydrous $Na_2SO_4$, filtered and concentrated under vacuum to yield (100%) crude product. This was stirred in 4.0M HCl/dioxane (40 mL) overnight and concentrated to afford the amine hydrochloride salt, from which the free base was liberated by treatment with a saturated $NaHCO_3$ solution. A THF solution of the amine (0.37 g, 1.1 mmol in 10 mL), triethylamine (0.15 mL, 1 equivalent) and the mixed anhydride formed from acetic anhydride/formic acid (1.1 mL) was stirred at 0° C. for 48 hours. The mixture was concentrated in vacuum, water (25 mL) added and the product extracted into dichloromethane (3×25 mL). The combined organics were washed with water (25 mL), saturated $NaHCO_3$ and dried over anhydrous sodium sulfate. Filtration and concentration in vacuum gave the required product (0.32 g, 80% yield). The bis-amide was reduced by the action of $BH_3.THF$ (10 equivalents) as described in example 8, and afforded the required amine (0.24 g, 88% yield) as a white solid. Cyclohexanecarboxylic acid chloride (0.1 g, 1.0 equivalents) was added to a solution of the amine (0.24 g, 0.7 mmol) and triethylamine (0.2 mL) in dichloromethane (5 mL) at 0° C. The mixture was allowed to stir under nitrogen overnight at ambient temperature, then concentrated under vacuum, diluted with ethyl acetate (50 mL) and washed with $H_2O$ (2×50 mL) then brine (50 mL). The organic phase was dried over anhydrous $Na_2SO_4$, filtered and concentrated under vacuum to yield the required amide. Purification by flash chromatography (elution with ethyl acetate/hexanes) yielded 0.31 g of the titled free base. The hydrochloride salt was prepared and crystallized yielding 0.21 g of the title compound as a white solid, m.p. 148–150° C.

Elemental Analysis for: $C_{28}H_{39}N_3O_2.2HCl.1.5H_2O$; Calculated: C, 61.19; H, 8.07; N, 7.65; Found: C, 61.18; H, 8;14; N, 7.57.

EXAMPLE 10

Cyclohexanecarboxylic acid {(1R)-2-[4-(2-Methoxy-phenyl)-piperidin-1-yl]-1-pyridin-4-ylmethyl-ethyl}-methyl-amide 1,2,3,6-Tetrahydro-4-(2-methoxyphenyl)pyridine (1.0 g, 4.39 mmol) was added to a solution of N-Boc-3'-(4'-pyridyl)-D-alanine (1.17 g, 4.39 mmol), DAEC (0.84 g, 4.39 mmol), and HOBT (0.77 g, 1.3 eq.) in DMF (20 mL) at 0° C., followed by the addition of NMO (0.7 mL, 1.5 eq.). The mixture was stirred under nitrogen overnight at ambient temperature, then diluted with ethyl acetate (50 mL), washed with 0.1N HCl (15 mL), saturated $NaHCO_3$, $H_2O$ and finally brine. The organic phase was dried over anhydrous $Na_2SO_4$, filtered and concentrated under vacuum to yield (100%) crude product. This was stirred in 4.0M HCl/dioxane (40 mL) overnight and concentrated to afford the amine hydrochloride salt, from which the free base was liberated by treatment with a saturated $NaHCO_3$ solution. A THF solution of the amine (0.5 g, 1.47 mmol in 10 mL), triethylamine (0.2 mL, 1 equivalent) and the mixed anhydride formed from acetic anhydride/formic acid (1.4 mL) was stirred at 0° C. for 48 hours. The mixture was concentrated in vacuum, water (25 mL) added and the product extracted into dichloromethane (3×25 mL). The combined organics were washed with water (25 mL), saturated $NaHCO_3$ and dried over anhydrous sodium sulfate. Filtration and concentration in vacuum gave the required product (0.38 g, 70% yield). The bis-amide was reduced by the action of $BH_3.THF$ (10 equivalents) as described in example 8, and afforded the required amine (0.24 g, 72% yield) as a white solid. Cyclohexanecarboxylic acid chloride (0.1 g, 1.0 equivalents) was added to a solution of the amine (0.24 g, 0.7 mmol) and triethylamine (0.2 mL) in dichloromethane (5 mL) at 0° C. The mixture was allowed to stir under nitrogen overnight at ambient temperature, then concentrated under vacuum, diluted with ethyl acetate (50 mL) and washed with $H_2O$ (2×50 mL) then brine (50 mL). The organic phase was dried over anhydrous $Na_2SO_4$ filtered and concentrated under vacuum to yield the required amide. Purification by flash chromatography (elution with ethyl acetate/hexanes) yielded 0.31 g (96% yield) of the titled free base. The hydrochloride salt was prepared and crystallized yielding 0.16 g of the title compound as a white solid, m.p. 158–160° C.

Elemental Analysis for: $C_{28}H_{39}N_3O_2.2HCl.1.75H_2O$; Calculated: C, 60.69; H, 8.10; N, 7.58; Found: C, 60.69; H, 8.32; N, 7.52.

EXAMPLE 11

(R)-Cyclohexanecarboxylic Acid {1-(4-Methoxybenzyl)-2-[4-(2-methoxy-phenyl)-piperidin-1-yl]-ethyl}-amide 1,2,3,6-Tetrahydro-4-(2-methoxyphenyl)pyridine (1.87 g, 8.29 mmol) was added to a solution of Boc-D-Tyr(OMe) (2.2 g, 7.54 mmol), 1-(3-dimethylaminopropyl)-3-ethylcarbodiimide (1.45 g, 7.54 mmol), and 1.53 g (11.3 mmol) of 1-hydroxybenzotriazole in DMF (20 mL) at 0° C., followed by the addition of 4-methylmorpholine (1.4 mL, 12.8 mmol). The mixture was stirred under nitrogen overnight at ambient temperature, then diluted with ethyl acetate (50 mL), washed with 0.1N HCl (15 mL), saturated $NaHCO_3$, $H_2O$ and finally brine. The organic phase was dried over anhydrous $Na_2SO_4$, filtered and concentrated under vacuum to yield (100%) crude product. This was stirred in 4.0M HCl/dioxane (40 mL) overnight and concentrated to afford the amine hydrochloride salt. The amide was dissolved in THF (50 mL) and reduced over 16 hours at 0° C. by the addition of 1.0M $LiAlH_4$/THF (23 mL). The reaction was quenched with the addition of saturated $NH_4Cl$, filtered through celite, dried over anhydrous $Na_2SO_4$, filtered and concentrated to yield the required product (1.3 g). Cyclohexanecarboxylic acid chloride (0.61 g, 4.13 mmol) was added to a solution of (1.3 g, 3.76 mmol) of crude amine and triethylamine (1.1 mL, 7.5 mmol) in of dichloromethane (20 mL) at 0° C. The mixture was allowed to stir under nitrogen overnight at ambient temperature, then concentrated under vacuum, diluted with ethyl acetate (50 mL) and washed with $H_2O$ (2×50 mL) then brine (50 mL). The organic phase was dried over anhydrous $Na_2SO_4$, filtered and concentrated under vacuum to yield the required amide. Purification by flash chromatography (elution with ethyl acetate/hexanes) yielded 0.64 g of the titled free base. The fumarate salt was prepared and crystallized yielding 0.27 g of the title compound as a pale yellow solid.

Elemental Analysis for: $C_{29}H_{40}N_2O_3 \cdot 1.0C_4H_4O_4$; Calculated: C, 68.25; H, 7.64; N, 4.82; Found: C, 68.19; H, 7.61; N, 4.84.

Compounds of the present invention bind with very high affinity to the 5-HT1A receptor and consequently, they are useful for the treatment of central nervous system disorders such as depression, anxiety, sleep disorders, sexual dysfunction, alcohol and cocaine addiction, cognition enhancement and related problems in addition to the treatment of Alzheimer's disease, Parkinson's disease, obesity and migraine.

5-HT1A Receptor Binding Assay

High affinity for the serotonin 5-HT1A receptor was established by testing the compound's ability to displace [$^3$H] 8-OH-DPAT bindino in CHO cells stably transfected with human 5HT1A receptor. Stably transfected CHO cells are grown in DMEM containing 10% heat inactivated FBS and non-essential amino acids. Cells are scraped off the plate, transferred to centrifuge tubes, and washed twice by centrifugation (2000 rpm for 10 min., 4° C.) in buffer (50 mM Tris pH 7.5). The resulting pellets are aliquoted and placed at −80° C. On the day of assay, the cells are thawed on ice and resuspended in buffer. The binding assay is performed in a 96 well microtiter plate in a total volume of 250 μL. Non-specific binding is determined in the presence of 10 mM 5-HT, final ligand concentration is 1.5 nM. Following a 30 minute incubation at room temperature, the reaction is terminated by the addition of ice cold buffer and rapid filtration through a GF/B filter presoaked for 30 minutes in 0.5% PEI. Compounds are initially tested in a single point assay to determine percent inhibition at 1, 0.1, and 0.01 mM, and Ki values are determined for the active compounds.

5-HT1A Receptor Intrinsic Activity Assay

The intrinsic activity of compounds of the present invention was established by testing the claimed compounds ability to reverse the stimulation of cyclic adenosinemonophosphate (cAMP) in CHO cells stably transfected with the human 5-HT1A receptor.

Stably transfected CHO cells were grown in DMEM containing 10% heat inactivated FBS and non-essential amino acids. The cells are plated at a density of ?×10$^6$ cells per well in a 24 well plate and incubated for 2 days in a $CO_2$ incubator. On the second day, the media is replaced with 0.5 mL treatment buffer (DMEM+25 mM HEPES, 5 mM theophylline, 10 μM pargyline) and incubated for 10 minutes at 37° C. Wells are treated with forskolin (1 μM final concentration) followed immediately by the test compound (0.1 and 1 μM for initial screen) and incubated for an additional 10 minutes at 37° C. The reaction is terminated by removal of the media and addition of 0.5 mL ice cold assay buffer (supplied in the RIA kit). Plates are stored at −20° C. prior to assessment of cAMP formation by RIA. $EC_{50}$ values are determined for the active test compounds. Compounds shown to have no agonist activities (Emax=0%) are further analyzed for their ability to reverse agonist-induced activity.

In separate experiments, 6 concentrations of antagonist are preincubated for 20 minutes prior to the addition of agonist and forskolin. Cells are harvested as described above. The cAMP kit is supplied by Amersham and the RIA is performed as per kit instructions, and calculations of $IC_{50}$ performed by GraphPad Prism.

| Compound | 5-HT1A binding Ki (nM) | cAMP $EC_{50}$ (nM) | Emax | $IC_{50}$ (nM) |
|---|---|---|---|---|
| Example 1 | 10.7 | — | 0% | 11.1 |
| Example 2 | 4.9 | — | 0% | |
| Example 3 | 0.22 | 3.4 | 84% | — |
| Example 4 | 0.25 | 4.3 | 84% | — |
| Example 5 | 0.24 | — | 0% | 0.29 |
| Example 6 | 0.23 | 16.9 | 92% | — |
| Example 7 | 0.74 | — | 0% | 38.0 |
| Example 8 | 0.63 | — | 0% | |
| Example 9 | 1.77 | — | 0% | |
| Example 10 | 1.18 | — | 0% | 19.3 |

Hence, compounds of the present invention exhibit high affinity for the 5HT1A receptor subtype and exhibit intrinsic activity as evidenced by their ability to reverse stimulation of cyclic adenosinemonophosphate (cAMP). Accordingly, compounds of the present invention are useful for treatment of disorders of the central nervous system and may be administered to a patient suffering from one or more of said disorders. Treatment, as used herein, refers to the alleviation or amelioration of symptoms of a particular disorder in a patient. In addition, compounds of the present invention may be administered as part of a treatment regime that includes other agents which act on the central nervous system. In some preferred embodiments, compounds of the present invention are part of a combination therapy including a serotonin reuptake inhibitor. Serotonin reuptake inhibitors useful in combination therapies of the present invention fluoxetine, fluvoxamine, paroxetine, sertraline and venlafaxine. Said agents may be administered at the same time, where they may be combined into a single dosage form, or at a different time, as compounds of the present invention, while still being part of the regime of the combination therapy.

Compounds of the invention may be administered to a patient either neat or with a convention pharmaceutical carrier.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of a specific psychosis must be subjectively determined by the attending physician. The variables involved include the specific psychosis or state of anxiety and the size, age and response pattern of the patient. The novel method of the invention for treating conditions related to or are affected by the 5-HT1A receptor comprise administering to warm-blooded animals, including humans, an effective amount of at least one compound of Formula A and its non-toxic, pharmaceutically acceptable addition salts. The compounds may be administered orally, rectally, parenterally or topically to the skin and mucosa. The usual daily dose is depending on the specific compound, method of treatment and condition treated. The usual daily dose is 0.01–1000 mg/Kg for oral application, preferably 0.5–500 mg/Kg, and 0.1–100 mg/Kg for parenteral application, preferably 0.5–50 mg/Kg.

What is claimed is:
1. A compound having the formula

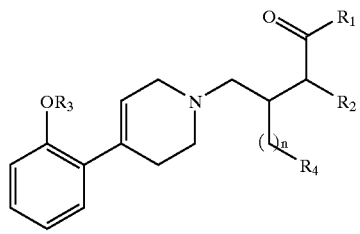

wherein:
$R_1$ is alkyl, cycloalkyl, alkylcycloalkyl, or aryl;
$R_2$ is hydrogen, or alkyl;
$R_3$ is alkyl;
X is hydrogen or halogen;
$R_4$ is phenyl or pyridyl; and
n is an integer from 1 to 3; or a pharmaceutically acceptable salt thereof.

2. A compound of claim 1 wherein $R_1$ is cycloalkyl of 3 to 8 carbon atoms.

3. A compound of claim 2 wherein said cycloalkyl is substituted with an alkyl of 1 to 6 carbon atoms.

4. A compound of claim 1 wherein X is 4-fluoro- or 5-fluoro-.

5. A compound of claim 1 wherein $R_4$ is phenyl, pyrid-3yl or pyrid-4yl.

6. A compound of claim 1 which is 1-methyl-cyclohexanecarboxylic acid {(1R)-1-benzyl-2-[4-(5-fluoro-2-methoxy-phenyl)-1,2,5,6-tetrahydro-4H-pyridin-1-yl]-ethyl}-methyl-amide, or a pharmaceutically acceptable salt thereof.

7. A compound of claim 1 which is (R)-Cyclohexanecarboxylic acid {1-benzyl-2-[4-(2-methoxy-phenyl)-3,6-dihydro-2H-pyridin-1-yl]-ethyl}-amide, or a pharmaceutically acceptable salt thereof.

8. A compound of claim 1 which is (R)-1-Methyl-cyclohexanecarboxylic acid{1-benzyl-2-[4-(2-methoxy-phenyl)-3,6-dihydro-2H-pyridin-1-yl]-ethyl}-amide, or a pharmaceutically acceptable salt thereof.

9. A pharmaceutical composition comprising a compound of claim 1 and a pharmaceutically acceptable carrier.

10. A method of treating a patient suffering from depression, anxiety or panic comprising administering to said patient a therapeutically effective amount of a compound having the formula

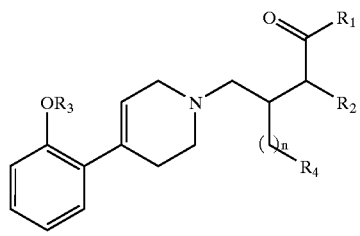

wherein:
$R_1$ is alkyl, cycloalkyl, alkylcycloalkyl, or aryl;
$R_2$ is hydrogen, or alkyl;
$R_3$ is alkyl;
X is hydrogen or halogen;
$R_4$ is phenyl or pyridyl; and
n is an integer from 1 to 3; or a pharmaceutically acceptable salt thereof.

11. The method of claim 10 wherein the patient is a human.

* * * * *